United States Patent [19]

Kino et al.

[11] Patent Number: 4,661,349

[45] Date of Patent: Apr. 28, 1987

[54] HERPES SIMPLEX VIRUS SUBUNIT VACCINE

[75] Inventors: Yoichiro Kino; Nobuya Ohtomo, both of Kumamoto, Japan

[73] Assignee: Juridicial Foundation, The Chemo-Sero-Therapeutic Research Institute, Japan

[21] Appl. No.: 883,736

[22] Filed: Jul. 9, 1986

Related U.S. Application Data

[63] Continuation of Ser. No. 643,268, Aug. 22, 1984, abandoned.

[30] Foreign Application Priority Data

Aug. 31, 1983 [JP] Japan ................... 58-159641

[51] Int. Cl.$^4$ ........................................... A61K 39/245
[52] U.S. Cl. ................................. 424/89; 435/235; 435/236; 435/238; 435/239
[58] Field of Search ............... 424/89; 435/7, 235-241

[56] References Cited

U.S. PATENT DOCUMENTS

| | | | |
|---|---|---|---|
| 4,317,811 | 3/1982 | Bertland et al. | 435/235 |
| 4,337,242 | 6/1982 | Markus et al. | 435/235 |
| 4,341,754 | 7/1982 | Kaplan et al. | 424/1.1 |
| 4,374,127 | 2/1983 | Larson et al. | 424/89 |
| 4,391,911 | 7/1983 | Tarro | 435/239 |
| 4,430,437 | 2/1984 | Hampar et al. | 435/241 |
| 4,452,734 | 6/1984 | Larson et al. | 260/112 R |
| 4,533,496 | 8/1985 | Lewis et al. | 435/240 |
| 4,535,057 | 8/1985 | Dreesman et al. | 435/810 |
| 4,540,669 | 9/1985 | Bertland et al. | 435/235 |

FOREIGN PATENT DOCUMENTS

| | | |
|---|---|---|
| 1365 | 4/1979 | European Pat. Off. . |
| 48201 | 3/1982 | European Pat. Off. . |
| 65905 | 12/1982 | European Pat. Off. . |
| 100521 | 2/1984 | European Pat. Off. . |
| 133063 | 2/1985 | European Pat. Off. . |
| 8302897 | 9/1983 | Int'l Pat. Institute . |

OTHER PUBLICATIONS

Skinner et al., Med. Microbiol. Immunol., 166, 119-132 (1978).
Kutinova et al., Arch. Virol., 61, 141-147, (1979).
Zweerink et al., Infec. Immun., 31, 267-275 (1981).
Klein et al., Arch. Virol., 68, 73-80, (1981).
Kitces et al., Infect. Immun., 16, 955-960, (1977).
Cappel et al., Arch. Virol., 65, 15-23, (1980).
Nahmias, A. J. et al., The Human Herpes Viruses, Elsevier, New York, 503-509 (1981).
Pereira et al., Pro. N.A.S., U.S.A., 78 5202-5206, (1981).
Kennett et al., Monoclonal Antibody, Plenum Press, New York, 363-419, (1981).
Eberle et al., J. Virol., 36, 665-675, (1980).
Balachandran et al., Infection and Immunity, vol. 37, No. 3, Sep. 1982, pp. 1132-1137, American Society for Microbiology, US;N.
R. J. Eisenberg et al., Chemical Abstracts, vol. 96, No. 21, May 24, 1982, p. 279, No. 176418p, Columbus, Ohio, US.
J. Glorioso et al., Chemical Abstracts, vol. 101, No. 3, Jul. 16, 1984, p. 457, No. 21720d, Columbus, Ohio, US.
R. E. Randall et al., Chemical Abstracts, vol. 99, No. 7, Aug. 15, 1983, p. 226, No. 49774p, Columbus, Ohio, US.
G. H. Cohen et al., Chemical Abstracts, vol. 78, No. 3, Jan. 22, 1973, p. 253, No. 14293v, Columbus, Ohio, US.

Primary Examiner—Shep K. Rose
Attorney, Agent, or Firm—Wegner & Bretschneider

[57] ABSTRACT

An improved herpes simplex virus subunit vaccine being effective against both of HSV type 1 and type 2 and having high safety and high effectiveness, which comprises as an active component a highly purified glycoprotein gB which is a component common to Herpes simplex virus type 1 and type 2, and a method for preparing the herpes simplex virus subunit vaccine and also a lyophilized preparation of the vaccine.

4 Claims, 1 Drawing Figure

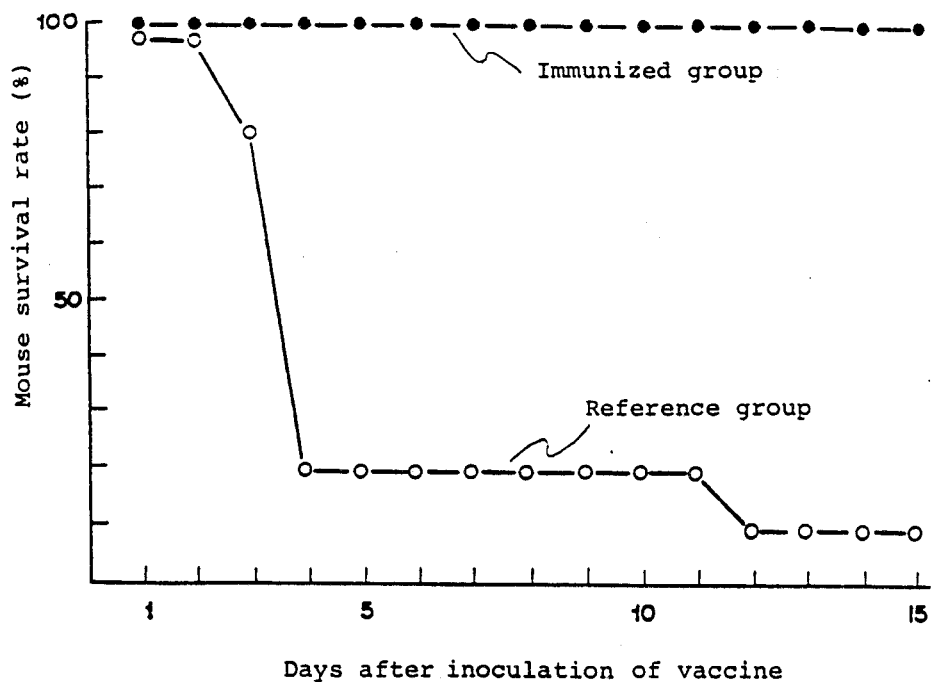

HERPES SIMPLEX VIRUS SUBUNIT VACCINE

This application is a continuation of Ser. No. 643,268, filed Aug. 22, 1984 now abandoned.

The present invention relates to a herpes simplex virus subunit vaccine. More particularly, it relates to a herpes simplex virus subunit vaccine which comprises as an effective component glycoprotein gB which is present in both herpes simplex virus type 1 and type 2 [Previously gB has been designated gA/B. Because gA and gB share antigenic determinants and gA can be changed into gB, it was agreed that the glycoprotein gA be designated pgB, a precursor to gB at the International Herpe Virus Workshop in Oxford England (1983)], said subunit vaccine being useful for prophilaxis of infection by herpes simplex virus type 1 and type 2.

TECHNICAL BACKGROUND AND FIELD IN INDUSTRY

Infectious diseases induced by various viruses are almost controlled by vaccination, but the prevention of infection due to herpes simplex virus is still a serious problem. In case of first infection in adult, the symptom is usually very heavy, and in developed countries, population having antibody against herpes simplex virus (hereinafter, referred to as "HSV") is decreasing. This problem will become more important in future. In some countries, it is taken into account as a kind of venereal disease or a neonatal herpes infection.

There are two types of virus in HSV, i.e. type 1 and type 2, and the type 1 virus infects mainly around lip, and the type 2 virus infects mainly around genitals.

It is known that both types of viruses are fairly distributed in Japan, and hence, it is important to take effective measures for prophylaxis of the virus infection in future.

Most effective prophylactic measures against virus infections are administration of a vaccine. However, in the case of HSV, development of vaccine is inhibited because of the specific properties of HSV, i.e. carcinogenicity and latent infection of the virus. It is very difficult to confirm that the infectiousness of HSV is removed in a live vaccine prepared from an attenuated virus or in an inactivated vaccine prepared by inactivating the virus by conventional inactivation processes, such as addition of inactivating agents or heat-treatment. If a viral infectiousness is remained in the vaccine, it may induce serious symptom to human body. When such a vaccine is innoculated to human, even though a symptom does not appear immediately, there is a possibility of latent infection. Thus, it is very difficult to prove the safety in HSV vaccine. In other aspect, the vaccine to be used for protection to the infection having low lethal rate such as herpes simplex infection must highly be purified in order to eliminate undesirable side effect. From these viewpoints, the conventional live vaccine and inactivated vaccine are not practically useful.

PRIOR ART

Under the circumstances, various studies have been done in order to develop a new vaccine having no danger of HSV infection due to vaccination, among which there are some reports on HSV subunit vaccine which might have a possibility of practical use.

It is known that specific glycoproteins of HSV are present in virus envelope which is surface region of HSV particles and also in the cell membrane of infected culture cells, and it has been considered that an antibody against the glycoproteins may be effective as an antibody for preventing HSV infection. Based on the assumption, it has been tried to use, for example, virus envelope components as a vaccine stock.

Skinner et al. have tried to use as a vaccine stock a part of fractions obtained from kidney cells of brephic hamster (BHK-21) infected with HSV type 1, which are prepared by destroying the kidney cells by ultrasonic treatment, dissolving the cells by adding thereto 1 v/v % of Nonidet P-40 (NP-40, manufactured by Shell Chemical), inactivating the virus by treating with formalin at 4° C. for 72 hours, and then subjecting the mixture to a cushion ultracentrifugation using 20 w/v % sucrose solution [cf. Med. Microbiol. Immunol., 166, 119–132 (1978)].

Kutinova et al. have tried to use as a vaccine stock a supernatant obtained from human embryonic lung cells infected with HSV type 1, which is prepared by adding 0.5 v/v % Nonidet P-40 to a suspension of the cells and thereby dissolving the cells, and removing nucleus substances of the cells and nucleocapsid of virus from the dissolved cells by centrifugation [cf. Arch. Virol., 61, 141–147 (1979)].

Zweerink et al. have reported to use as a vaccine stock a component of a primary kidney cells of rabbit infected with HSV type 1, which is prepared by dissolving the kidney cells infected with HSV type 1 with Tris-EDTA buffer containing 1 v/v % Triton X-100, removing the nucleus substances of the cells by low speed centrifugation, removing high molecular weight substances by high speed centrifugation, passing the resulting supernatant through an affinity column packed with Sepharose 4B bound with lentil lectin, and eluting the adsorbed components with an eluting solution containing α-methylmannoside and glucose [cf. Infect. Immun., 31, 267–275 (1981)].

Bertland et al. have used as a vaccine stock a virus envelope from chicken embryo fibroblast infected with HSV type 1, which is prepared by dissolving the chicken embryo fibroblast with a phosphate buffer containing 4 mole of urea, separating the cell components by continuous ultracentrifugation, inactivating the virus components contained in the supernatant by subjecting it to ultrasonic treatment and heat treatment at 60° C. for 3 hours, decomposing the virus DNA with deoxyribonuclease, and subjecting the resultant to gel filtration chromatography with Sepharose Cl-6B to remove deoxyribonuclease, by which the virus envelope components is isolated [cf. U.S. Pat. No. 4,317,811 (1982)].

Another aspect has been done by Klein et al. [cf. Arch. Virol., 68, 73–80 (1981)], that is, a culture supernatant of Vero cells infected with HSV type 1 is subjected to continuous ultracentrifugation with sucrose density gradient to obtain purified virus particles, and a suspension of the virus particles is treated with 1 v/v % Triton X-100 to destroy the virus particles, and then the resultant is subjected to ultracentrifugation with sucrose density gradient to separate into HSV nucleocapsid and virus envelope component, and the latter component is used as a vaccine stock.

Kitces et al. have used as a vaccine stock a virus envelope component having no HSV-originated nucleic acid obtained from human pharyngeal cancer epithelial cells (Hep-2 cells) infected with HSV type 1, which is prepared by destroying the epithelial cells with homogenizer, centrifuging the homogenized mixture to separate a supernatant of virus particle suspension, subjecting the supernatant to inactivation with formalin, adding 1 w/v % of sodium dodecylsulfate and N-lauroylsurcosine sodium salt to the virus particle suspension in order to dissolve them, subjecting the mixture to ultracentrifugation with cesium chloride to collect a nucleocapsid-free supernatant, treating it with deoxyribonuclease to give the desired virus envelope having no nucleic acid [cf. Infect. Immun., 16, 955–960 (1977)].

Cappel et al. have tried to use as a vaccine stock a virus envelope component from chicken embryo fibroblast infected with HSV type 1, which is prepared by subjecting repeatedly the cells to ultrasonic treatment and freezing-thawing in order to destroy the cells, subjecting the resulting mixture to a low centrifugation and ultrafiltration to partially purify the virus particles, subjecting the crude virus particles to sugar density gradient ultracentrifugation twice to give purified virus particles, dissolving the particles with 1 v/v % Nonidet P-40, and subjecting the solution to sugar solution cusion ultracentrifugation to collect the desired virus envelope component.

The above reports are all concerned with HSV type 1, and as to HSV type 2, it is also reported by Hilleman et al. that a subunit vaccine is obtained by subjecting chicken embryo fibroblast infected with HSV type 2 to dissolving treatment with Triton X-100, treating the mixture with deoxyribonuclease, subjecting the mixture to lectine-affinity chromatography and Sepharose gel filtration to collect virus glycoproteins and then treating it with aluminum gel [cf. The Human Herpes Viruses, 503–509, by Nahmias, A. J. et al., Elsevier, N.Y. (1981)].

In these reports, partially purified virus envelope is used as the virus stock and is treated with aluminum hydroxide gel in order to incease immunogenicity. It has experimentally been confirmed in mice that the virus envelope is effective as a virus stock, but the process for the preparation thereof is very complicated in the purification step, and further, the purification is not sufficient and hence it is contaminated with culture cell components.

It is very important, as mentioned above, that a vaccine for HSV must be highly purified in order to avoid undesirable side effect as low as possible. It is assumed that the known vaccines are contaminated with a fairly amount of proteins from the host, even through the vaccine stock is obtained by extracting it from infected cells or virus particles. Thus, the known vaccines are hardly acceptable as an HSV subunit vaccine for human in view of less safety.

The vaccine stock used for a subunit vaccine against HSV should most preferably have antigenic determinants common to HSV type 1 and type 2 and the antigenicity is not sufficient by mere producibility of neutralizing antibody against the virus but should be capable of completely prohibiting the HSV infection. Moreover, as is mentioned above, the vaccine product should have high safety and excellent effectiveness and also sufficient storage stability in the form of a vaccine preparation. Thus, the practical HSV vaccine product should be prepared from a purified vaccine stock having a specified component and be effective against both HSV type 1 and type 2.

HSV type 1 and type 2 are different not only in serological viewpoint but also in some biological properties. However, DNA thereof is similar to each other in about 50%, and the proteins thereof are also fairly overlapped in both. Besides, it is said that they have a common antigen. As is mentioned above, the antigens responsible for resistance to HSV infection is present in the virus envelope, and glycoproteins contained therein are particularly noticed. At Cold Spring Harbor Workshop in 1979 (cf. The Human Herpes Viruses, 503–509 (1981), ed. by Nahmias et al., Elsevier, N.Y.), Spear et al. have proposed that various glycoproteins contained in the HVS envelope component are classified and designated gC (molecualr weight: 130,000), gB (90,000–115,000), gE (60,000–80,000), and gD (58,000).

Among the above fractions, gB is contained in the largest amount, gC and gD are the next, and gE is the smallest one. It is said that both of gC and gE can produce a neutralizing antibody, but these are type specific and that gB and gD can produce a nutralizing antibody which neutralizes both type 1 and type 2. It is also reported that gC can protect HSV infection.

BRIEF SUMMARY OF THE INVENTION

Based on the knowledge that gB is contained in the HSV envelope in the largest amount and is common between the type 1 and type 2 and produce a neutralizing antibody reactive to both types of HSV, the present inventors have studied on gB. It has been found that among the subunit glycoproteins present in the HSV envelope, gB, which is glycoprotein common to both HSV type 1 and type 2, can exhibit immunological activity sufficient for preventing infection of the both types of HSV and the gB can easily be isolated and purified by an improved method.

An object of the present invention is to provide an improved HSV subunit vaccine effective against both of HSV type 1 and type 2. Another object of the invention is to provide a HSV subunit vaccine having high safety and high effectiveness which comprises as an active component highly purified glycoprotein gB. A further object of the invention is to provide a method for preparing a HSV subunit vaccine. A still further object of the invention is to provide a method for purifying the glycoprotein gB. These objects and advantages of the invention will be apparent to those skilled in the art from the following description.

BRIEF DESCRIPTION OF THE DRAWING

The FIGURE shows the correlation between mouse survival rate and days after inoculation of vaccine in the Experiment below.

DETAILED EXPLANATION

The highly purified glycoprotein gB can be prepared by subjecting a solution containing HSV specific subunit glycoproteins to affinity chromatography using a monoclonal antibody as a ligand.

The solution containing HSV specific subunit glycoproteins includes lysate of mammalian cells infected with HSV (including both of type 1 and type 2, unless specified otherwise), lysate of partially purified HSV particles from the culture cells, which are obtained by dissolving HSV specific subunit glycoproteins with a surfactant, or an organic solvent.

The culture cells infected with HSV express HSV specific subunit glycoproteins on the cell membrane as well as virus particle, and these culture cells can be used as the starting material in the present invention. Besides, there can also be used recombinant culture cells being capable of producing HSV gB which are obtained by genetic engineering technique.

HSV can propagate in wide range of hosts, and the natural host is human, but HSV can also infect to and can be grown in monkey, rabbit, guinea pig, hamster, mouse, rat and grown hen's egg, etc. Thus, various mammalian cells sensitive to HSV can be used in the present invention. For example, brephic hamster kidney cells (BHK-21), Green monkey kidney cells (Vero), human embryonic lung cells (HEL), human pharyngeal cancer epithelial cells (Hep-2), primary rabbit kidney cells (PRK), chicken embryo fibroblast, or the like are usable in the present invention.

For isolating the desired gB, the starting material may optionally be subjected to pretreatment. For example, the HSV-infected culture cells or the culture supernatant is subjected to the treatment with a homogenizer or ultrasonic treatment to destroy the cells and then the resulting HSV-containing solution is centrifuged to remove crude insoluble materials such as cell pieces to give a dispersion of purified HSV particles. The thus obtained HSV particles dispersion may also be subjected to the affinity chromatography of the present invention.

The surfactant used for dissolving the subunit glycoproteins includes anion surfactants such as sodium dodecylsulfate (SDS), sodium deoxycholate, and non-ionic surfactants such as Triton X-100 (tradename of polyoxyethylene ether manufactured by Rohm and Haas Co.), Nonidet P-40 (tradeneme of octylphenoxy-polyethoxyethanol, manufactured by Shell Company), Tween-20 (tradename of polyoxyethylene sorbitan monolaurate, manufactured by Bio-Rad), but preferably nonionic surfactants. The addition amount of the surfactant is usually 0.1 to 10 v/v %, preferably 0.5 to 2.0 v/v %.

The dissolving treatment is usually carried out by adding a required amount of a surfactant to a dispersion of HSV specific subunit glycoproteins and allowing to stand or stirring the mixture at a temperature of 0° to 25° C. for 24 hours.

The glycoproteins dissolved and extracted by the above dissoving treatment are re-combined unless any surfactant is present in the system, and hence, the glycoproteins-containing solution is subjected to the affinity chromatography with a ligand of a monoclonal antibody against the HSV glycoproteins gB in the presence of 0.01 to 0.1 v/v % of an anionic surfactant or a non-ionic surfactant, by which the desired gB is isolated.

When a lectine is used as a ligand for the affinity chromatography, other glycoproteins originated from the cells as well as the gB are all adsorbed, and hence, the desired gB is not so highly purified. On the other hand, when a monoclonal antibody to gB is used as the ligand, the gB can be bound with a high specificity, and hence, the desired gB can be purified in a high degree.

The purification of gB by the affinity chromatography using a monoclonal antibody as the ligand can be carried out by the steps consisting of passing a solution containing dissolved glycoproteins gB through an affinity gel equilibrated with an approximately neutral buffer (e.g. M/100 phosphate buffer, pH 7.2) which contains 0.01 to 0.1 v/v % of an anionic or nonionic surfactant, washing the gel adsorbed with gB with the above-mentioned buffer, eluting out the gB by passing through an eluting solution, such as 3M potassium thiocyanate aqueous solution, 3M sodium thiocyanate aqueous solution, 5M magnesium chloride aqueous solution, 6M urea aqueous solution, which contains 0.01 to 0.1 v/v % of a nonionic surfactant, and then dialyzing the eluate against an approximately neutral buffer (e.g. M/100 phosphate buffer, pH 7.2, or Tris-HCl buffer, pH 7.4) containing 0.01 to 0.1 v/v % of a nonionic surfactant to give the desired solution containing purified gB.

The gB thus obtained have the following physio chemical properties.

The lyophilized product thereof has white, amorphous powder. It has a solubility of about 10 % in M/100 phosphate-buffered saline solution (PBS) (pH 7.2) containing 0.05 v/v % of Triton X-100. When an aqueous solution of the gB is heated at 60° C. for 60 minutes, the antigenicity is not lost.

It shows blue color (as a peptide) by Lourie-Foline reaction, and when hydrolyzed, it shows violet blue color (as an α-amino acid) by Ninhydrin reaction.

It has a molecular weight of about 90,000 when measured by electrophoresis with SDS-polyacrylamide gel and of about 95,000 when measured by gel filtration analysis with Cellulofine GC-700 (a tradename of a cellulose derivative, manufactured by Chisso Corporation).

The amino acid components of gB was determined after hydrolyzed by an automatic amino acid analyzer. The kinds of the amino acids and the number of amino acid residue calculated per one molecule of gB are as follows: lysine (40), histidine (20), arginine (51), aspartic acid (86), threonine (55), serine (55), glutamic acid (91), glycine (73), alanine (79), cysteine (1), valine (60), methionine (17), isoleucine (40), leucine (66), thyrosine (33), and phenylalanine (40). Triptophane could not be measured by the above method.

The gB prepared by the present invention do not contain any impurity in the analysis by an electrophoresis with SDS-polyacrylamide gel and by immunoblotting method.

Vaccine preparation is usually prepared by adding an immuno adjuvant (e.g. aluminum gel) in order to enhance the antibody producibility when vaccinated. The vacccine preparation incorporated aluminum gel is prepared after regulating the protein content of the purified gB to the range of not more than 0.1 w/v %, preferably not more than 0.02 w/v %, usually 0.02 to 0.04 w/v %, with an approximately neutral buffer (e.g. phosphate buffered saline pH 7.2) or with a physiological saline solution. Aluminum gel for adsorbing gB is used in an amount of 3 to 10 times by weight as much as the amount of gB.

The adsorption of gB onto aluminum gel is usually carried out by adding an aluminum gel-containing solution to a gB-containing solution, or by adding a fixed amount of an aluminum chloride-containing solution to a gB-containing solution and therto adding an aqueous solution of sodium hydroxide having an appropriate concentration, by which aluminum hydroxide gel is produced and simultaneously gB is adsorbed to the produced gel. In the latter process, an aqueous solution of trisodium phosphate may be used instead of an aqueous solution of sodium hydroxide, by which the gB is adsorbed onto the produced aluminum phosphate gel. Thus, the aluminum gel used in the present invention includes aluminum hydroxide gel and aluminum phosphate gel.

To the gB-adsorbed aluminum gel suspension obtained above is added a preservative (e.g. thimerosal) in an amount of 0.005 to 0.1 w/v % to give the aluminum gel-added vaccine preparation.

The gB-adsorbed aluminum gel suspension may be mixed with a stabilizer and optionally a preservative, and then the mixture is lyophilized.

The stabilizer includes amino acids and saccharides, which are used either one alone or preferably used together, and further preferably, colloidal materials are used as a stabilizer together with the amino acids and saccharides. The kinds of the stabilizers and amount thereof are not specifically restricted, but all materials are usable in an amount which is used for the conventional lyophilized vaccine preparations.

Suitable examples of the amino acids are glycine, alanine, glutaminic acid, arginine, lysine, etc. or a salt thereof (e.g. monosodium glutamate). They may be used alone or in combination of two or more thereof, and they are usually used in an amount of 0.1 to 2.0 w/v %. Suitable examples of saccharides are monosaccharides such as glucose, xylose, galactose, fructose, etc., disaccharides such as lactose, maltose, saccharose, etc., and sugar alcohols such as mannitol, sorbitol, xylithol, etc., which may be used alone or in combination of two or more thereof. They are usually used in an amount of 0.1 to 15 w/v %. Suitable examples of colloidal substances are gelatin, human albumin, dextrane, etc. They are usually used in an amount of 0 to 0.1 w/v %.

The purified gB-containing solution incorporated with a stabilizer is divided and poured into small vessels so that a fixed amount of gB is contained in each vessel, i.e. in a dosage unit of 20 μg to 40 μg in each vessel. The divided solution in each vessel is lyophilized by conventional rapid lyophilization or slow lyophilization to give a lyophilized preparation. The lyophilization is usually carried out under the following conditions. For example, the solution is subjected to a pre-lyophilization at a low temperature (e.g. −40° C. or lower, preferably −50° C. or lower) under atmospheric pressure for several hours (e.g. 3 to 10 hours), and then subjected to first lyophilization at a fixed higher temperature (e.g. 0° to 8° C.) under a reduced pressure (e.g. 0.01 to 0.05 Torr) for ten to a few tens of hours (e.g. 15 hours), at which stage the temperature of the product becomes lower than −35° C. (e.g. about −38° C.). Thereafter, the prouct is subjected to second lyophilization at a fixed elevated temperature (e.g. 25° to 30° C.) under a reduced pressure (e.g. 0.05 to 0.005 Torr) for several to ten hours (e.g. 6 to 10 hours, preferably 7 to 9 hours).

The lyophilized preparation of HSV subunit vaccine thus obtained can be kept with good storage stability without lowering of antigen titer and further can be dissolved rapidly in an injection solution when used.

When the lyophilized preparation of the present invention is used, it is dissolved in distilled water for injection or physiological saline solution for injection so as to regulate the gB protein concentration to 20μg to 40 μg, and the physiologically isotonic solution is administered in subcutaneous or intramuscular route. The dose of the vaccine is usually in the range of 20 μg to 40 μg as gB protein for one administration in adult.

The present invention is illustrated by the following Preparation and Examples, but should not be construed to be limited thereto.

PREPARATION

Preparation of monoclonal antibody:

Vero cells infected with HSV type 1 KOS strain is collected 24 hours after infection, and are dissolved by treating with PBS (pH 7.2–7.4) containing 1 v/v % Triton X-100 at 4° C. for one hour. The dissolved solution is centrifuged at 100,000 G for one hour, and then, the supernatant is collected to give crude glycoprotein fraction. This fraction (0.1 ml, protein amount: 100 mg/ml) is intracutaneously inoculated to a hind footpad of BALB/c (4 weeks old, female) to immunize the animals. One month after the immunization, the spleen is taken out and sliced, to which is added Eagle MEN medium to give an immunized spleen cell dispersion.

The immunized spleen cell suspension (cell number, $1 \times 10^8$ cells) and a separately prepared P3U1 cell suspension (cell number, $1 \times 10^7$ cells) are added to a tube and the mixture is subjected to cell-fuse reaction using polyethylene glycol 4,000 at 37° C. for 5 minutes. The resulting hybridoma is selected with HAT medium [cf. Monoclonal Antibody, ed. by Kennett et al., 2nd. Ed., Plenum Press, N.Y. 363–419 (1981)]. Among the selected hybridoma, a hybridoma being capable of producing an antibody against gB is selected. The thus obtained hybridoma is intraperitoneally transplanted to BALB/C female mouse (4 weeks old) treated with 2,6,10,14-tetramethylpentadecane (manufactured by Aldrich Chemical Co.). Seven to 14 days after the transplantation, the ascitic fluid is collected to obtain a monoclonal antibody against gB (amount of IgG: 10 mg/ml).

EXAMPLE 1

(1) Preparation of column bound with monoclonal antibody:

To the ascitic fluid containing monoclonal antibody obtained in the above Preparation is added 50 % ammonium sulfate at 4° C. to precipitate IgG fraction, which is dissolved in a cuppling buffer (0.05 mole $Na_2HCO_3$, 0.15 mole NaCl, pH 8.2).

The solution is dialyzed against the same buffer as used above at 4° C. for 24 hours, and thereafter, is bound to CNBr-activated Sepharose 4B (manufactured by Pharmacia) in a concentration of 5 mg/ml to give an antibody-bound column.

(2) Purification of gB with the antibody-bound column:

Vero cells are infected with HSV type 1 KOS strain, and 24 hours after the infection the cells are collected. The cells are dissolved with PBS (pH 7.2–7.4) containing 1 v/v % Triton X-100 and then passed through the antibody-bound column. The column is washed with PBS (pH 7.2–7.4) containing 0.05 v/v % Triton X-100 and then passed through with 3 moles KSCN to elute the adsorbed gB. The eluate is dialyzed against PBS (pH 7.2–7.4) containing 0.05 v/v % Triton X-100 and concentrated by ultrafiltration. These operations are carried out at 4° C.

The purified gB is analyzed by electrophoresis using SDS-polyacrylamide gel. As a result, there are observed the main band of gB at around 90 K and also several bonds at around 45 K. When the proteins are blotted on a nitrocellulose paper and are reacted with a monoclonal antibody and an anti-HSV rabbit serum, respectively. As a result, both of the band at 90 K and that at 45 K are reacted with both antibodies.

In view of the result of blotting as mentioned above, the band at 45 K which is observed by the electrophoresis with SDS-polyacrylamide gel may be decomposed products of gB which are obtained by decomposing with an enzyme originated from Vero cells, as is reported by Pereira et al [cf. Pro. Natl. Acad. Sci., USA, 78, 5202 (1981)].

EXAMPLE 2

Preparation of a vaccine from the purified gB:

A solution of the purified gB in PBS (pH 7.2–7.4) containing 0.05 v/v % Triton X-100 (protein content: 30 μg/ml) is mixed with an aqueous solution of aluminum chloride (corresponding to aluminum hydroxide in 8 times by weight as much as the amount of the gB protein). The mixture is regulated to pH 6.7 with 1N NaOH, by which aluminum hydroxide gel is produced and simultaneously gB is adsorbed thereon. The gB-adsorbed aluminum gel is centrifuged, and the supanatant is removed. The precipitates are again dispersed in PBS (pH 7.2–7.4), wherein the amount of gB is regulated to a concentration of 30,μg/ml, to give an aluminum gel-treated vaccine stock. Thimerosal (a preservative) is added thereto in an amount of 0.01 w/v %, and the mixture is divided and poured into 2 ml vials (each content: 1 ml), and the vials are each sealed and stored. When the vials are allowed to stand, white, cloud-like precipitates are produced, and the supernatant is clear. When it is lightly shaken, it becomes easily uniform white suspension.

EXAMPLE 3

Preparation of lyophilized vaccine from purified gB:

Precipitates of gB-adsorbed aluminum gel obtained in the same manner as described in Example 2 are again dispersed in a physiological saline solution (pH 7.2–7.4) containing lactose 10 w/v %, monosodium 1-glutaminate 0.4 w/v %, arginine 0.4 w/v %, gelatine 0.8 w/v % and thimerosal 0.005 w/v %, wherein the concentration of gB is regulated to 30 μg/ml, to give a vaccine stock for lyophilization. The vaccine stock is divided and poured into 2 ml vials (each content: 1 ml), and then subjected to pre-lyophilization at −50° C., under atmospheric pressure for 6 hours, to the first lyophilization at 5° C., under reduced pressure of 0.04 Torr for 15 minutes, and then to the second lyophilization at 30° C., under a reduced pressure of 0.05 Torr for 8 hours to give a lyophilized vaccine product.

EXPERIMENT

Safety and immunogenicity of a vaccine from purified gB:

(1) The vaccine prepared in Example 2 was intracutaneously inoculated into a hind footpad of BALB/c female mice (4 weeks old, 10 mice) in an amount of 0.1 ml (gB protein content: 3 μg). Two and three weeks after the first immunization, a vaccine which was not treated with aluminum gel was inoculated in the same amount in order to additionally immunize. To control mice (10 mice), PBS (pH 7.2–7.4) was inoculated likewise. During these treatments, all mice were fine without any lowering of body weight and appetite and any other abnormal behavior.

One week after the final immunization, HSV type 1 Hayashida strain (clinically isolated highly toxic strain, $LD_{50}$: less than $10^3$ PFU) was intraperitoneally inoculated in an amount of $1 \times 10^8$ PFU/0.1 ml. The survival ratio with the lapse of time was shown in the accompanying FIGURE. That is, in the reference group, a mouse was died even after 3 days and the total death rate was such a high as 90 %. on the contrary, in the immunized group, no mouse was died even 2 months after the challenge.

(2) The vaccine prepared in Example 2 was used for immunization of BALB/c female mice (4 week old, 10 mice) in the same manner as described in the above 1). In both of immunized group and reference group, there was observed no abnormality. One week after the final immunization, HSV type 2 8204TN strain (clinically isolated highly toxic strain, $LD_{50}$: less than $10_2$ PFU) was intraperitoneally inoculated in an amount of $1 \times 10^5$ PFU/0.1 ml. As a result, in the reference group, the total death rate was such a high as 80 %, but in the immunized group, no mouse was died even 2 months after the challenge.

(3) The lyophilized vaccine prepared in Example 3 was used for immunization of BALB/c female mice (4 week old, 10 mice) in the same manner as described in the above 1). In both of immunized group and reference group, there was observed no abnormality. One week after the final immunization, HSV type 1 Hayashida strain was intraperitoneally inoculated in an amount of $1 \times 10^8$ PFU/0.1 ml. As a result, in the immunized group, no mouse was died even 2 months after th attack, while in the reference group, the total death rate was such a high as 90 %.

(4) The preparations of the present invention prepared in Examples 2 and 3 were subjected to the test for checking the abnomality and toxicity using guinea pigs in accordance with the method as defined in Minimum Requirement of Biological Products (issued by the Ministry of Health and Welfare, Japan, July, 1979). As a result, no abnormality was observed.

What is claimed is:

1. A method for preparing a herpes simplex subunit vaccine, which comprises subjecting a solution containing herpes simplex virus glycoproteins to affinity chromatography using as a ligand a monoclonal antibody against herpes simplex virus glycoprotein gB, and adsorbing the resulting purified glycoprotein gB onto an aluminum gel to obtain a glycoprotein gB-adsorbed aluminum gel dispersion.

2. The method according to claim 1, wherein the solution containing herpes simplex virus glycoproteins is a solution obtained by subjecting particles of herpes simplex virus type 1 or type 2 or a virus envelope component of cells infected with the virus to dissolving treatment with a surfactant.

3. A herpes simplex virus subunit vaccine, which comprises as an essential active component glycoprotein gB produced by the method of subjecting a solution containing herpes simplex virus glycoproteins to affinity chromatography using as a ligand a monoclonal antibody against herpes simplex virus glycoprotein gB, and adsorbing the resulting purified glycoprotein gB onto an aluminum gel to obtain a glycoprotein gB-adsorbed aluminum gel dispersion.

4. The vaccine according to claim 3, wherein the solution containing herpes simplex virus glycoproteins is a solution obtained by subjecting particles of herpes simplex virus type 1 or type 2 or a virus envelope component of cells infected with the virus to dissolving treatment with a surfactant.

* * * * *